(12) United States Patent
Clark et al.

(10) Patent No.: US 6,655,379 B2
(45) Date of Patent: Dec. 2, 2003

(54) AEROSOLIZED ACTIVE AGENT DELIVERY

(75) Inventors: Andrew Clark, Half Moon Bay, CA (US); George H. Foulds, Chester, CT (US)

(73) Assignee: Nektar Therapeutics, San Carlos, CA (US)

( * ) Notice: Subject to any disclaimer, the term of this patent is extended or adjusted under 35 U.S.C. 154(b) by 4 days.

(21) Appl. No.: 09/266,720

(22) Filed: Mar. 11, 1999

(65) Prior Publication Data

US 2003/0183228 A1 Oct. 2, 2003

Related U.S. Application Data (60) Provisional application No. 60/078,212, filed on Mar. 16, 1998, and provisional application No. 60/078,214, filed on Mar. 16, 1998.

(51) Int. Cl.[7] .............................................. A61M 16/00
(52) U.S. Cl. .............................. 128/203.12; 128/205.24
(58) Field of Search ....................... 128/205.24, 203.12, 128/200.23; 600/529, 533, 532, 538, 539, 540; 482/13

(56) References Cited

U.S. PATENT DOCUMENTS

| | | | | |
|---|---|---|---|---|
| 393,869 | A | * 12/1888 | Warren | 128/203.24 |
| 957,548 | A | * 5/1910 | Doane | 128/203.24 |
| 2,586,215 | A | 2/1952 | Priestly | |
| 2,788,784 | A | * 4/1957 | Birch et al. | 128/200.23 |
| 3,788,310 | A | * 1/1974 | Fleischmann | 128/142 |
| 3,837,341 | A | 9/1974 | Bell | |
| 3,991,304 | A | * 11/1976 | Hillsman | 600/538 |
| 4,086,918 | A | 5/1978 | Russo | |
| 4,106,503 | A | 8/1978 | Rosenthal et al. | |
| 4,114,608 | A | 9/1978 | Russo | |
| 4,170,228 | A | 10/1979 | Elson et al. | |
| 4,259,951 | A | 4/1981 | Chernack et al. | |
| 4,274,404 | A | * 6/1981 | Molzan et al. | 128/204.25 |
| 4,284,083 | A | 8/1981 | Lester | |
| 4,338,931 | A | 7/1982 | Cavazza | |
| 4,366,947 | A | * 1/1983 | Voege | 251/206 |
| 4,391,283 | A | 7/1983 | Sharpless et al. | |
| 4,442,856 | A | * 4/1984 | Betz | 137/98 |
| 4,444,202 | A | 4/1984 | Rubin et al. | |
| 4,484,577 | A | * 11/1984 | Sackner et al. | 128/203.28 |

(List continued on next page.)

FOREIGN PATENT DOCUMENTS

| | | |
|---|---|---|
| EP | 808635 | 11/1997 |
| EP | 714314 | 10/1998 |
| EP | 805696 | 3/2000 |
| GB | 1598053 | 9/1981 |
| WO | 91/14422 | 10/1991 |

(List continued on next page.)

OTHER PUBLICATIONS

Ross DL et al., ""Effect of Inhalation Flow Rate on the Dosing Characteristics of Dry Power Inahle (MDI) Products"," J. Aerosol Med: Deposition, Clearance and Effects in the Lung, vol. 9 (No. 2), (Oct. 25, 1996).

Lawford P et al., ""Pressurized Aerosol Inhaler Technique: How Improtant are Inhalation from Residual Volume, Inspiratory Flow Rate and the Time between Puffs?"," Br. J. Dis. Chest, vol. 77 (No. 3), p. 276–281, (Jul. 25, 1983).

Elliott et al., Aust. Paediatr. J., p. 293–297, (1987).

(List continued on next page.)

*Primary Examiner*—Weilun Lo
*Assistant Examiner*—Mital Patel
(74) *Attorney, Agent, or Firm*—Guy V. Tucker; Felissa H. Cagan

(57) ABSTRACT

The present invention is directed to methods and devices for delivering an active agent formulation to the lung of a human patient. The active agent formulation may be in dry powder form, it may be nebulized, or it may be in admixture with a propellant. The active agent formulation is delivered to a patient at an inspiratory flow rate of less than 17 liters per minute. The bioavailability of the active agent was found to increase at these flow rates when compared to inspiratory flow rates of 17 liters per minute or more.

25 Claims, 3 Drawing Sheets

U.S. PATENT DOCUMENTS

| | | | |
|---|---|---|---|
| 4,495,944 A | | 1/1985 | Brisson et al. |
| 4,533,137 A | | 8/1985 | Sonne |
| 4,558,710 A | | 12/1985 | Eichler |
| 4,592,348 A | | 6/1986 | Waters, IV et al. |
| 4,627,432 A | | 12/1986 | Newell et al. |
| 4,677,975 A | | 7/1987 | Edgar et al. |
| 4,778,054 A | | 10/1988 | Newell et al. |
| 4,811,731 A | | 3/1989 | Newell et al. |
| 4,907,583 A | | 3/1990 | Wetterlin et al. |
| 4,926,852 A | * | 5/1990 | Zoltan et al. .......... 128/200.23 |
| 4,955,371 A | | 9/1990 | Zamba et al. |
| 4,991,745 A | | 2/1991 | Brown |
| 5,027,806 A | | 7/1991 | Zoltan et al. |
| 5,033,655 A | | 7/1991 | Brown |
| 5,040,527 A | | 8/1991 | Larson et al. |
| 5,042,467 A | | 8/1991 | Foley |
| 5,042,472 A | | 8/1991 | Bunin |
| 5,161,524 A | | 11/1992 | Evans |
| 5,167,506 A | | 12/1992 | Kilis et al. |
| 5,184,641 A | | 2/1993 | Kuhn |
| 5,201,308 A | | 4/1993 | Newhouse |
| 5,213,236 A | | 5/1993 | Brown et al. |
| 5,284,133 A | | 2/1994 | Burns et al. |
| 5,301,666 A | | 4/1994 | Lerk et al. |
| 5,320,094 A | | 6/1994 | Laube et al. |
| 5,333,106 A | | 7/1994 | Lanpher et al. |
| 5,337,740 A | | 8/1994 | Armstrong et al. |
| 5,339,995 A | | 8/1994 | Brown et al. |
| 5,364,838 A | | 11/1994 | Rubsamen |
| 5,377,877 A | | 1/1995 | Brown et al. |
| 5,385,140 A | | 1/1995 | Smith |
| 5,408,994 A | | 4/1995 | Wass et al. |
| 5,409,144 A | | 4/1995 | Brown |
| 5,419,315 A | | 5/1995 | Rubsamen |
| 5,435,301 A | | 7/1995 | Herold et al. |
| 5,437,271 A | | 8/1995 | Hodson et al. |
| 5,439,143 A | | 8/1995 | Brown et al. |
| 5,447,151 A | | 9/1995 | Bruna et al. |
| 5,458,135 A | * | 10/1995 | Patton et al. .......... 128/200.14 |
| 5,483,954 A | | 1/1996 | Mecikalski |
| 5,509,404 A | | 4/1996 | Lloyd et al. |
| 5,513,630 A | | 5/1996 | Century |
| 5,522,380 A | | 6/1996 | Dwork |
| 5,529,059 A | | 6/1996 | Armstrong et al. |
| 5,533,505 A | | 7/1996 | Kallstrand et al. |
| 5,542,412 A | | 8/1996 | Century |
| 5,558,085 A | | 9/1996 | Rubsamen et al. |
| 5,568,807 A | | 10/1996 | Mecikalski |
| 5,568,910 A | * | 10/1996 | Koehler et al. ........ 128/205.24 |
| 5,586,550 A | | 12/1996 | Ivri et al. |
| 5,603,315 A | * | 2/1997 | Sasso, Jr. ............... 128/202.22 |
| 5,617,845 A | | 4/1997 | Poss et al. |
| 5,622,166 A | | 4/1997 | Eisele et al. |
| 5,653,223 A | | 8/1997 | Pruitt |
| 5,654,007 A | | 8/1997 | Johnson et al. |
| 5,655,520 A | | 8/1997 | Howe et al. |
| 5,672,581 A | | 9/1997 | Rubsamen et al. |
| 5,692,492 A | | 12/1997 | Bruna et al. |
| 5,692,496 A | | 12/1997 | Casper et al. |
| 5,699,789 A | | 12/1997 | Hendricks |
| 5,724,959 A | | 3/1998 | McAughey et al. |
| 5,727,546 A | | 3/1998 | Clarke et al. |
| 5,740,794 A | | 4/1998 | Smith et al. |
| 5,775,320 A | | 7/1998 | Patton et al. |
| 5,785,049 A | | 7/1998 | Smith et al. |
| 5,813,401 A | | 9/1998 | Radcliff et al. |
| 5,823,183 A | | 10/1998 | Casper et al. |
| 5,826,571 A | | 10/1998 | Casper et al. |
| 5,826,633 A | | 10/1998 | Parks et al. |
| 5,839,430 A | * | 11/1998 | Cama .................... 128/200.14 |
| 5,855,202 A | | 1/1999 | Andrade |
| 5,873,358 A | | 2/1999 | Gonda et al. |
| 5,875,776 A | | 3/1999 | Vaghefi |
| 5,881,719 A | | 3/1999 | Gottenauer et al. |
| 5,884,620 A | | 3/1999 | Gonda et al. |
| 5,896,853 A | | 4/1999 | Howlett |
| 5,921,237 A | | 7/1999 | Eisele et al. |
| 5,922,354 A | | 7/1999 | Johnson et al. |
| 5,941,240 A | * | 8/1999 | Gonda et al. .......... 128/200.14 |
| 5,975,076 A | | 11/1999 | Yianneskis et al. |
| 5,983,893 A | | 11/1999 | Wetterlin |
| 5,988,163 A | | 11/1999 | Casper et al. |
| 5,993,421 A | * | 11/1999 | Kriesel ....................... 604/132 |
| 6,006,747 A | | 12/1999 | Eisele et al. |
| 6,012,454 A | | 1/2000 | Hodson et al. |
| 6,029,661 A | | 2/2000 | Whaley et al. |
| 6,029,663 A | | 2/2000 | Eisele et al. |
| 6,032,667 A | * | 3/2000 | Heinonen ............... 128/203.12 |
| 6,055,979 A | | 5/2000 | Fuchs |
| 6,055,980 A | | 5/2000 | Mecikalski et al. |
| 6,065,472 A | | 5/2000 | Anderson et al. |
| 6,067,984 A | * | 5/2000 | Piper ..................... 128/204.18 |
| 6,070,573 A | | 6/2000 | Howe et al. |
| 6,076,523 A | * | 6/2000 | Jones et al. ............ 128/205.11 |
| 6,085,753 A | | 7/2000 | Gonda et al. |
| 6,089,228 A | | 7/2000 | Smith et al. |
| 6,095,134 A | * | 8/2000 | Sievers et al. ......... 128/200.14 |
| 6,102,036 A | | 8/2000 | Slutsky et al. |
| 6,105,574 A | | 8/2000 | Jahnsson |
| 6,109,261 A | | 8/2000 | Clarke et al. |
| 6,116,237 A | | 9/2000 | Schultz et al. |
| 6,116,238 A | | 9/2000 | Jackson et al. |
| 6,116,239 A | | 9/2000 | Volgyesi |
| 6,131,571 A | * | 10/2000 | Lampotang et al. ... 128/204.18 |
| 6,138,673 A | | 10/2000 | Shepherd |
| 6,142,146 A | | 11/2000 | Abrams et al. |
| 6,186,142 B1 | * | 2/2001 | Schmidt et al. ........ 128/204.18 |
| 6,253,764 B1 | * | 7/2001 | Calluaud ................ 128/204.18 |
| 6,286,506 B1 | * | 9/2001 | MacAndrew et al. .. 128/203.15 |

FOREIGN PATENT DOCUMENTS

| | | |
|---|---|---|
| WO | WO 95/24183 | 9/1995 |
| WO | 95/34337 | 12/1995 |
| WO | WO 96/09085 | 3/1996 |
| WO | WO 96/30068 | 10/1996 |
| WO | WO 96/32149 | 10/1996 |
| WO | 97/40819 | 11/1997 |
| WO | 98/32479 | 7/1998 |
| WO | 99/27987 | 6/1999 |
| WO | 99/46055 | 6/1999 |
| WO | 99/47196 | 9/1999 |
| WO | 00/21594 | 4/2000 |

OTHER PUBLICATIONS

Prime et al., "The Flixotide Diskus™, a new multi dose powder inhaler–consistency of dose and fine particle mass, protein from moisture." Abstract from Journal of Aerosol Medicine, 8, P138, 1995.

Prime et al., "The Flixotide Diskus™, a new multi dose powder inhaler–in vitro evaluation using an inhalation simulator." Abstract from Journal of Aerosol Medicine, 8, P137, 1995.

Robertson et al., "The influence of (pseudo) polymorphic forms of lactose on dry powder inhaler performance." Abstract from Journal of Aerosol Medicine, 8, P139, 1995.

Conway et al., "Comparison of peak Pressure Drops Through Powder Inhalers During Inspiration at Maximum Flow Rate" Abstract from American Journal of Respiratory and Critical Care Medicine, vol. 153, No. 4, A59, Apr. 1996.

Newhouse et al. "Clickhaler (a Novel Dry Power Inhaler) Provides Similar Bronchodilation to Pressurized Metered-Dose Inhaler, Even at Low Flow Rates" Clinical Investigations, Chest, 115, 4, pp. 952–956, Apr. 1999.

Chrystyn, "The Diskus Inhaler, A Review of its Pharmaceutical and Clinical Performance", Clinical drug Investigations, 18(4): 287–296, 1999.

Clark, "Effect of Powder Inhaler Resistance Upon Inspiratory Profiles in Health and Disease", Respiratory Drug Delivery, IV, pp. 117–123, 1994.

Clark et al., "The Relationship Between Powder Inhaler Resistance and Peak Inspiratory Conditions in Healthy Volunteers—Implications for in Vitro Testing" Journal of Aerosol Medicine, vol. 6, No. 2, pp. 99–110, 1993.

Dolovich, "Physical Principles Underlying Aerosol Therapy" Journal of Aerosol Medicine, vol. 2, No. 2, pp. 171–186, 1989.

Hill, "Characteristics of an Active, Multiple Dose Dry Powder Inhaler" Respiratory Drug Delivery IV, pp. 109–116, 1994.

Barrowcliff et al. "The In–Vitro Evaluation of a Novel Multi–Dose Dry Powder Inhaler", The Aerosol Society, pp. 82–85, 1996.

Malton et al., "A comparison of in–vitro drug delivery from salbutamol Diskus and terbutaline Turbohaler inhalers" J. Pharm, Med. 6, pp. 35–48, 1996.

Malton et al., "A comparison of in vitro drug delivery from two multidose powder inhalation devices" European Journal of Clinical Research, 7, pp. 177–193, 1995.

* cited by examiner

AEROSOLIZED ACTIVE AGENT DELIVERY

This application claims priority to U.S. Provisional Patent Application Serial No. 60/078,212 and U.S. Provisional Patent Application Serial No. 60/078,214, both of which were filed on Mar. 16, 1998.

FIELD OF THE INVENTION

The present invention is related to the pulmonary delivery of an active agent formulation. More particularly, it is a method and device for pulmonary delivery of an active agent formulation for increased systemic bioavailability of the active agent via absorption in the deep lung. Average inspiratory flow rates of less than 17 liters per minute of active agent formulation must be maintained in order to achieve increased bioavailability.

BACKGROUND OF THE INVENTION

Effective delivery to a patient is a critical aspect of any successful drug therapy. Various routes of delivery exist, and each has its own advantages and disadvantages. Oral drug delivery of pills, capsules, elixirs, and the like is perhaps the most convenient method, but many drugs are degraded in the digestive tract before they can be absorbed. Subcutaneous injection is frequently an effective route for systemic drug delivery, including the delivery of proteins, but enjoys a low patient acceptance. Since injection of drugs, such as insulin, one or more times a day can frequently be a source of poor patient compliance, a variety of alternative routes of administration have also been developed, including transdermal, intranasal, intrarectal, intravaginal, and pulmonary delivery.

Insulin is a 50 amino acid polypeptide hormone having a molecular weight of about 6,000 daltons which is produced in the pancreatic β-cells of normal (non-diabetic) individuals. Insulin is necessary for regulating carbohydrate metabolism by reducing blood glucose levels. Where the body's ability to regulate blood glucose levels has been impaired, diabetes will result. There are two main types of diabetes. In Type I, the insulin-secreting cells of the pancreas are destroyed. Insulin production is therefore nearly completely halted. In Type II, either the body produces insulin but in quantities that are insufficient to regulate blood sugar levels to within a normal range or the insulin receptors are unable to adequately process the insulin in the blood. Survival of Type I diabetic patients depends on the frequent and long-term administration of insulin to maintain acceptable blood glucose levels. Type II diabetics may require insulin administration, but diet, exercise or oral medications are often used to avoid the necessity of daily injections of insulin.

Insulin is most commonly administered by subcutaneous injection, typically into the abdomen or upper thighs. In order to maintain acceptable blood glucose levels, it is often necessary to inject basal insulin at least once or twice per day, with supplemental injections of rapid-acting insulin being administered when necessary, usually prior to meals. Blood glucose levels should typically remain between 50 mg/dl and 300 mg/dl, preferably between about 80 mg/dl and 120 mg/dl with a target blood glucose level of 100 mg/dl. Aggressive treatment of diabetes can require even more frequent injections, in conjunction with the close monitoring of blood glucose levels by patients using home diagnostic kits.

The administration of insulin by injection is undesirable in a number of respects. First, many patients find it difficult and burdensome to inject themselves as frequently as necessary to maintain acceptable blood glucose levels. Such reluctance can lead to non-compliance with recommended therapeutic regimens, which in the most serious cases can be life-threatening. Moreover, systemic absorption of insulin from subcutaneous injection is relatively slow when compared to the normal release of insulin by the pancreas, frequently requiring from 45 to 90 minutes, even when fast-acting insulin formulations are employed. Thus, it has long been a goal to provide alternative insulin formulations and routes of administration which avoid the need for physically invasive injections and which can provide rapid systemic blood levels of the insulin as seen in normal subjects.

Elliot et al, Aust. Paediatr. J.(1987)23:293–297 described the nebulized delivery of semi-synthetic human insulin to the respiratory tracts of six diabetic children and determined that it was possible to control diabetes in these children, although the efficiency of absorption was low (20–25%) as compared to subcutaneous delivery. Laube et al., U.S. Pat. No. 5,320,094, noting Elliot and a number of other studies, stressed that although insulin had been delivered to the lung, none of the patients had responded to the pulmonary insulin therapy sufficient for lowering of blood glucose levels to within a normal range. Laube et al. hypothesized that this problem resulted from the loss of drug in the delivery system and/or in the oropharynx as a result of the method of delivery and that the maximization of deposition within the lungs should improve glucose control in the blood. In order to achieve maximum delivery, Laube et al controlled the inspiratory flow rate at the time of aerosol inhalation at flow rates of less than 30 liters/minute and, preferably about 17 liters/minute. The delivery system included a medication chamber for receiving the insulin, an outlet aperture through which the insulin was withdrawn, and a flow rate limiting aperture to control the inspiratory flow rate.

Rubsamen et al, U.S. Pat. Nos. 5,364,838 and 5,672,581 describe the delivery of a measured amount of aerosolized insulin. The insulin is automatically released into the inspiratory flow path in response to information obtained from determining the inspiratory flow rate and inspiratory volume of a patient. A monitoring device continually sends information to a microprocessor, and when the microprocessor determines that an optimal point in the respiratory cycle is reached, the microprocessor actuates the opening of a valve allowing release of insulin. The inspiratory flow rate is in the range of from about 0.1 to 2.0 liters/second and the volume is in the range of from about 0.1 to 0.8 liters.

Even with the amount of work that has been done to optimize delivery of inhaled insulin, there has not been a system and method of delivery that has provided sufficient delivery of insulin to the lung for maintaining target blood glucose levels in diabetic patients. Such a system and method for delivery would be useful for the delivery of many other active agents as well.

SUMMARY OF THE INVENTION

Accordingly, in one aspect, the present invention is directed to a method for delivering an active agent formulation to the lungs of a human patient, said method comprising providing the active agent formulation at an inspiratory flow rate of below 17 liters per minute. The active agent formulation may be provided in dry powder or nebulized form, or it may be in the form of aerosolized particles in admixture with a propellant.

In another aspect, the present invention is directed to a method for delivering insulin to the lungs of a human patient, said method comprising providing insulin at an inspiratory flow rate of below 17 liters per minute. The is preferably provided in dry powder form, but it may also be in nebulized form, or it may be in the form of aerosolized particles in admixture with a propellant.

In yet another aspect, the present invention is directed to a device for increasing the bioavailability of an aerosolized active agent, said device comprising a flow restricter for limiting the flow of the aerosolized active agent formulation to below 17 liters per minute. The flow restricter may be in the form of a simple orifice, a valve that provides for increasing resistance with increasing flow rate, a valve that provides for decreasing resistance with increasing flow rate, or a valve that provides for high resistance at all flow rates except the desired flow rate.

In a further aspect, the present invention is directed to a device for delivering an active agent to the lungs of a human patient wherein the device delivers an aerosolized active agent formulation at an inspiratory flow rate of less than 17 liters per minute.

The present invention is also directed to a device for delivering insulin to the lungs of a human patient wherein the device delivers an aerosolized insulin formulation at an inspiratory flow rate of less than 17 liters per minute.

DESCRIPTION OF THE FIGURES

FIG. 1A is a perspective view and

FIG. 2A is a cross-sectional view and

FIG. 3A is a perspective view and

DETAILED DESCRIPTION OF THE INVENTION

The present invention provides a method and device for the pulmonary delivery of an active agent formulation where inspiratory flow rate of the active agent formulation is less than 17 liters/min. The invention is surprising in that it provides for increased blood levels of active agent than observed following higher inspiratory flow rates.

Definitions

"Active agent" as described herein includes an agent, drug, compound, composition of matter or mixture there which provides some pharmacologic, often beneficial, effect. This includes foods, food supplements, nutrients, drugs, vaccines, vitamins, and other beneficial agents. As used herein, the terms further include any physiologically or pharmacologically active substance that produces a localized or systemic effect in a patient. The active agent that can be delivered includes antibiotics, antiviral agents, anepileptics, analgesics, anti-inflammatory agents and bronchodilators, and may be inorganic and organic compounds, including, without limitation, drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletel system, autacoid systems, the alimentary and excretory systems, the histamine system the central nervous system. Suitable agents may be selected from, for example, polysaccharides, steroid, hypnotics and sedatives, psychic energizers, tranquilizers, anticonvulsants, muscle relaxants, antiparkinson agents, analgesics, anti-inflammatories, muscle contractants, antimicrobials, antimalarials, hormonal agents including contraceptives, sympathomimetics, polypeptides, and proteins capable of eliciting physiological effects, diuretics, lipid regulating agents, antiandrogenic agents, antiparasitics, neoplastics, antineoplastics, hypoglycemics, nutritional agents and supplements, growth supplements, fats, antienteritis agents, electrolytes, vaccines and diagnostic agents.

Examples of active agents useful in this invention include but are not limited to insulin, calcitonin, erythropoietin (EPO), Factor VIII, Factor IX, ceredase, cerezyme, cyclosporin, granulocyte colony stimulating factor (GCSF), alpha-1 proteinase inhibitor, elcatonin, granulocyte macrophage colony stimulating factor (GMCSF), growth hormone, human growth hormone (HGH), growth hormone releasing hormone (GHRH), heparin, low molecular weight heparin (LMWH), interferon alpha, interferon beta, interferon gamma, interleukin-2, luteinizing hormone releasing hormone (LHRH), somatostatin, somatostatin analogs including octreotide, vasopressin analog, follicle stimulating hormone (FSH), insulin-like growth factor, insulintropin, interleukin-1 receptor antagonist, interleukin-3, interleukin-4, interleukin-6, macrophage colony stimulating factor (M-CSF), nerve growth factor, parathyroid hormone (PTH), thymosin alpha 1, IIb/IIIa inhibitor, alpha-1 antitrypsin, respiratory syncytial virus antibody, cystic fibrosis transmembrane regulator (CFTR) gene, deoxyreibonuclease (Dnase), bactericidal/permeability increasing protein (BPI), anti-CMV antibody, interleukin-1 receptor, 13-cis retinoic acid, pentamidine isethiouate, albuterol sulfate, metaproterenol sulfate, beclomethasone diprepionate, triamcinolone acetamide, budesonide acetonide, ipratropium bromide, flunisolide, fluticasone, cromolyn sodium, ergotamine tartrate and the analogues, agonists and antagonists of the above. Active agents may further comprise nucleic acids, present as bare nucleic acid molecules, viral vectors, associated viral particles, nucleic acids associated or incorporated within lipids or a lipid-containing material, plasmid DNA or RNA or other nucleic acid construction of a type suitable for transfection or transformation of cells, particularly cells of the alveolar regions of the lungs. The active agents may be in various forms, such as soluble and insoluble charged or uncharged molecules, components of molecular complexes or pharmacologically acceptable salts. The active agents may be naturally occurring molecules or they may be recombinantly produced, or they may be analogs of the naturally occurring or recombinantly produced active agents with one or more amino acids added or deleted. Further, the active agent may comprise live attenuated or killed viruses suitable for use as vaccines. Where the active agent is insulin, the term includes natural extracted human insulin, recombinantly produced human insulin, insulin extracted from bovine and/or porcine sources, recombinantly produced porcine and bovine insulin and mixtures of any of the above. The insulin may be neat, that is in its substantially purified form, but may also include excipients as commercially formulated. Also included in the term "insulin" are insulin analogs where one or more of the amino acids of the naturally occurring or recombinantly produced insulin has been deleted or added.

"Aerosolized active agent formulation" means the active agent as defined above in a formulation that is suitable for pulmonary delivery. The aerosolized active agent formulation may be in the dry powder form, it may be a solution, suspension or slurry to be nebulized, or it may be in admixture with a suitable low boiling point, highly volatile propellant. It is to be understood that more than one active agent may be incorporated into the aerosolized active agent formulation and that the use of the term "agent" in no way excludes the use of two or more such agents.

The "inspiratory flow rate" or "average inspiratory flow rate" are used interchangeably here to mean the flow rate at which the aerosolized active agent formulation is delivered. For a continuous nebulizer, this is the flow rate over the entire breath. For a device that gives an aerosol bolus, such as a dry powder inhaler or an MDI, this is the average flow rate throughout the period during which the aerosol bolus. is delivered plus the time taken for the aerosol to traverse the anatomical dead space, i.e. from the lips to beyond generation 6 or 8 of the airways (approximately 150 mls).

The amount of active agent in the aerosolized active agent formulation will be that amount necessary to deliver a therapeutically effective amount of the active agent to achieve the desired result. In practice, this will vary widely depending upon the particular agent, the severity of the condition, and the desired therapeutic effect. However, the device is generally useful for active agents that must be delivered in doses of from 0.001 mg/day to 100 mg/day, preferably 0.01 mg/day to 50 mg/day.

The present invention is based at least in part on the unexpected observation that when an active agent is delivered to a patient at an inspiratory flow rate of less than 17 liters per minute or preferably less than 12 liters per minute and more preferably 10 liters per minute or less and often between 5 and 10 liters per minute, the lung deposition and thus the bioavailability of the active agent increases as opposed to when the active agent is delivered at an inspiratory flow rate of 17 liters per minute or more. It was surprising that the lower flow rate would lead to a higher bioavailability since Laube et al (U.S. Pat. No. 5,320,094) determined the optimal flow rate of aerosolized insulin to be 17 liters per minute and that up to 30 liters per minute was desirable.

Active agent formulations suitable for use in the present invention include dry powders, solutions. suspensions or slurries for nebulization and particles suspended or dissolved within a propellant. Dry powders suitable for use in the present invention include amorphous active agents, crystalline active agents and mixtures of both amorphous and crystalline active agents. The dry powder active agents have al particle size selected to permit penetration into the alveoli of the lungs, that is, preferably less than 10 $\mu$m mass median diameter (MMD), preferably less than 7.5 $\mu$m, and most preferably less than 5 $\mu$m, and usually being in the range of 0.1 $\mu$m to 5 $\mu$m in diameter. The delivered dose efficiency (DDE) of these powders is >30%, usually >40%, preferably >50 and often >60% and the aerosol particle size distribution is about 1.0–5.0 $\mu$m mass median aerodynamic diameter (MMAD), usually 1.5–4.5 $\mu$m MMAD and preferably 1.5–4.0 $\mu$m MMAD. These dry powder active agents have a moisture content below about 10% by weight, usually below about 5% by weight, and preferably below about 3% by weight. Such active agent powders are described in WO 95/24183 and WO 96/32149, which are incorporated by reference herein.

Dry powder active agent formulations are preferably prepared by spray drying under conditions which result in a substantially amorphous powder. Bulk active agent, usually in crystalline form, is dissolved in a physiologically acceptable aqueous buffer, typically a citrate buffer having a pH range from about 2 to 9. The active agent is dissolved at a concentration from 0.01% by weight to 1% by weight, usually from 0.1% to 0.2%. The solutions may then be spray dried in a conventional spray drier available from commercial suppliers such as Niro A/S (Denmark), Buchi (Switzerland) and the like, resulting in a substantially amorphous powder. These amorphous powders may also be prepared by lyophilization, vacuum drying, or evaporative drying of a suitable active agent solution under conditions to produce the amorphous structure. The amorphous active agent formulation so produced can be ground or milled to produce particles within the desired size range. Dry powder active agents may also be in a crystalline form. The crystalline dry powders may be prepared by grinding or jet milling the bulk crystalline active agent.

The active agent powders of the present invention may optionally be combined with pharmaceutical carriers or excipients which are suitable for respiratory and pulmonary administration. Such carriers may serve simply as bulking agents when it is desired to reduce the active agent concentration in the powder which is being delivered to a patient, but may also serve to improve the dispersability of the powder within a powder dispersion device in order to provide more efficient and reproducible delivery of the active agent and to improve handling characteristic of the active agent such as flowability and consistency to facilitate manufacturing and powder filling. Such excipients include but are not limited to (a) carbohydrates, e.g., monosaccharides such as fructose, galactose, glucose, D-mannose, sorbose, and the like; disaccharides, such as lactose, trehalose, cellobiose, and the like; cyclodextrins, such as 2-hydroxypropyl-β-cyclodextrin; and polysaccharides, such as raffinose, maltodextrins, dextrans, and the like; (b) amino acids, such as glycine, arginine, aspartic acid, glutamic acid, cysteine, lysine, and the like; (c) organic salts prepared from organic acids and bases, such as sodium citrate, sodium ascorbate, magnesium gluconate, sodium gluconate, tromethamin hydrochloride, and the like; (d) peptides and proteins such as aspartame, human serum albumin, gelatin, and the like; and (e) alditols, such as mannitol, xylitol, and the like. A preferred group of carriers includes lactose, trehalose, raffinose, maltodextrins, glycine, sodium citrate, human serum albumin and mannitol.

The dry powder active agent formulations may be delivered using Inhale Therapeutic Systems' dry powder inhaler as described in WO 96/09085 which is incorporated herein by reference, but adapted to control the flow rate to 17 liters per minute or less as described below. The dry powders may also be delivered using a metered dose inhaler as described by Laube et al in U.S. Pat. No. 5,320,094, which is incorporated by reference herein.

Nebulized solutions may be prepared by aerosolizing commercially available active agent formulation solutions. These solutions may be delivered by a jet nebulizer such as the Raindrop, produced by Puritan Bennett, the use of which is described by Laube et al. Other methods for delivery of solutions, suspensions of slurries are described by Rubsamen et al, U.S. Pat. No. 5,672,581. A device that uses a vibrating, piezoelectric member is described in Ivri et al, U.S. Pat. No. 5,586,550. which is incorporated by reference herein.

Propellant systems may include an active agent dissolved in a propellant or particles suspended in a propellant. Both of these types of formulations are described in Rubsamen et al, U.S. Pat. No. 5,672,581, which is incorporated herein by reference.

Figure 1A:
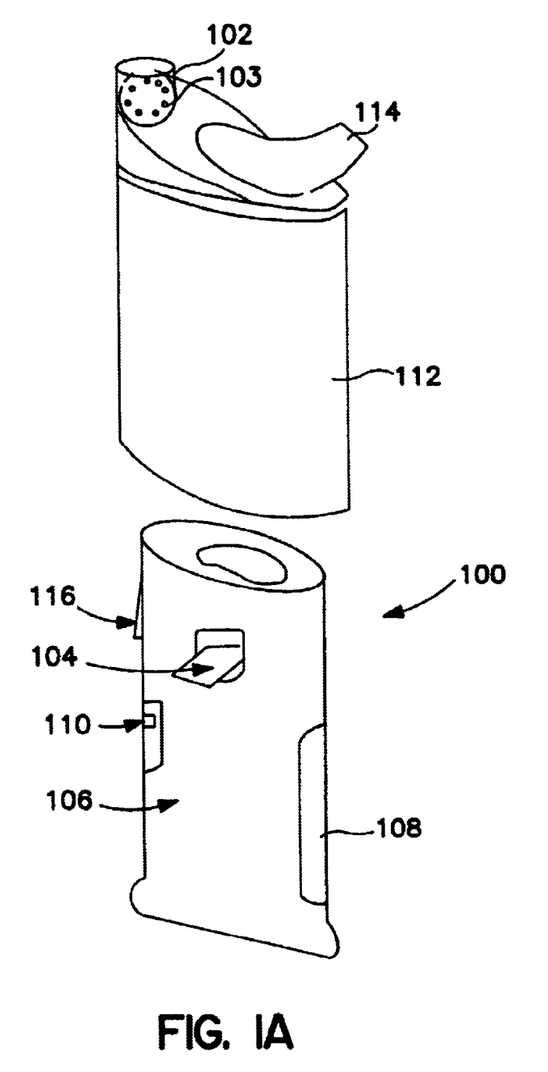
Figure 1B:
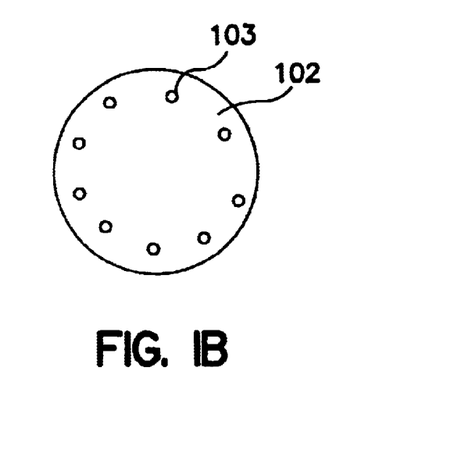
FIG. 1B is an elevational view of an embodiment of a dry powder active agent formulation delivery device of the invention.

In order to obtain the increased bioavailabilities of active agent, the devices described above must be modified in order to restrict the inspiratory flow rate of the active agent formulation to 10 liters per minute or less. FIGS. 1A, 1B, 2A, 2B, 3A, 3B, 4A and 4B show this restriction achieved by devices using a simple orifice. FIGS. 5A, 5B, 6A, 6B, 7A and 7B show alternative flow control methods useful in any of the FIGS. 1A, 2A or 3A devices. With regard to the devices for delivering the dry powder active agent formulation as shown in FIGS. 1A and 1B, the device 100 contains a flow restricter 102 with apertures 103 that limits the inspiratory flow to 10 liters per minute or less according to the invention. FIG. 1A shows an exploded view of the device described in WO 96/09085. Briefly, a patient inserts a blister of active agent into the base 106 of the device. The handle 108 is cocked to compress air for dispersion of the active agent. Lever 110 is lowered to lift the blister 104 into place. Button 116 is depressed which punctures the blister 104 and releases the active agent with the compressed air into the capture chamber 112. The patient puts his mouth over mouthpiece 114 and the aerosolized active agent formulation is withdrawn through flow restricter 102 at a rate of 10 liters per minute or less.

Figure 2A:
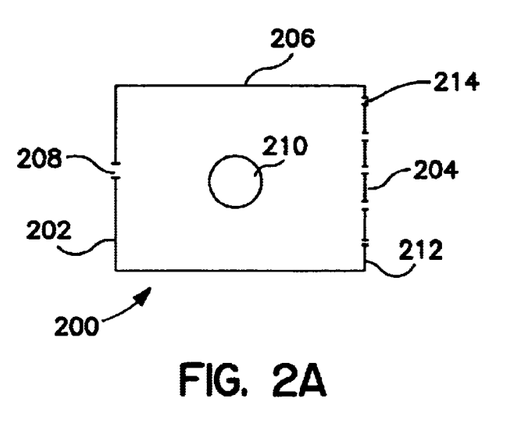
Figure 2B:
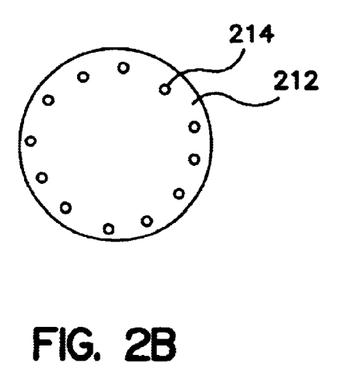
FIG. 2B is an elevational view of an embodiment of a nebulized active agent formulation delivery device of the invention.

FIGS. 2A and 2B show a rigid chamber 200 suitable for restricting the inspiratory flow rate delivered by a nebulizer according to the invention. As described in Laube et al, a rigid chamber 200 is provided having a proximal end 202, a distal end 204 and a main body 206. The proximal end 202 has an aperture 208 that is sized to accept standard disposable mouthpieces for use with hospital nebulizers. The body of the device 206 has an opening has an opening 210 of a size suitable for coupling to an external source of aerosolized active agent. The aerosolized active agent formulation is delivered to the chamber 200 through opening 210. The opening 210 is then covered such that the aerosolized active agent is contained within the chamber 200. The distal end 204 contains a flow restricter 212. in this case a series of apertures 214 such that when a patient inhales the active agent formulation through a mouthpiece attached to the aperture 208, the inspiratory flow rate of the active agent formulation is maintained at or below 10 liters per minute.

Figure 3A:
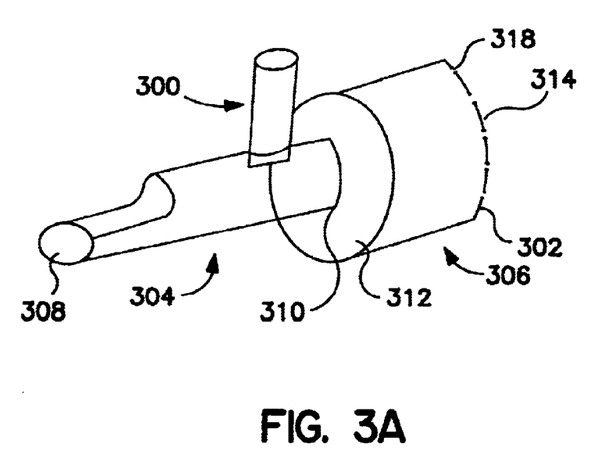
Figure 3B:
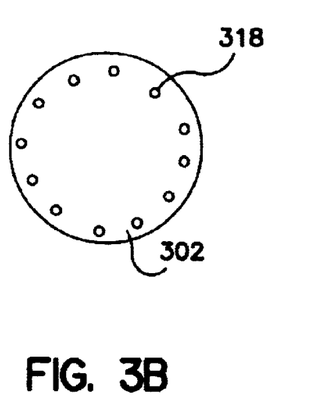
FIG. 3B is an elevational view of an embodiment of a propellant driven active agent formulation delivery device of the invention.

In order to restrict the inspiratory flow rate on a propellant driven system, a metered dose inhaler (MDI) 300 may be provided with a flow restricter 302 as shown in FIGS. 3A and 3B and further described in Laube et al. The MDI 300 is shown with a mouthpiece 304 and a rigid chamber 306. The proximal end 308 of the mouthpiece 304 is adapted to be placed in the mouth of a patient. The distal end 310 of the mouthpiece 304 is rigidly attached to the proximal end 312 of chamber 306. The MDI is attached such that when operated, a dose of aerosolized active agent formulation is released into chamber 306. The distal end 314 of chamber 306 contains a flow restricter 302, in this case a series of apertures 318 as shown in FIG. 3B, such that when a patient inhales the active agent formulation through the proximal end 308 of the mouthpiece 304, the inspiratory flow rate of the active agent formulation is maintained at or below 10 liters per minute.

Figures 4A, 4B:
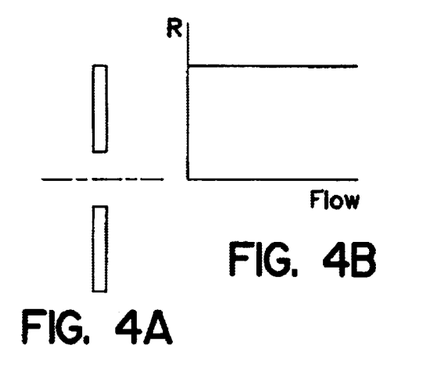
FIG. 4A is a perspective view of a simple orifice.
FIG. 4B is a graph showing the type of resistance obtained therefrom.

The devices of FIGS. 1–3 use a simple orifice as shown in FIG. 4A to achieve the desired inspiratory flow rate. The rate of air flow through the orifice is proportional to the square root of the pressure drop across it, and in this case the resistance (R) is constant as shown in FIG. 4B. In order to obtain a flow rate of 10 liters per minute, the resistance required is approximately 1 cm $H_2O^{1/2}/Lmin^{-1}$. This is accomplished by including a flow restricter with a total orifice area of approximately 2 to 4 $mm^2$. In the embodiments shown in FIGS. 1–3, there are 8–12 apertures of 0.5–0.9 mm diameter which will provide for this type of flow.

Figure 5A:
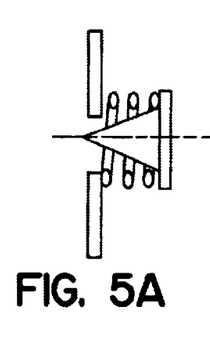
FIG. 5A is a perspective view of a valve that provides for increasing resistance with increasing flow rate and FIG. 5B is a graph showing the type of resistance obtained therefrom.
Figure 5B:
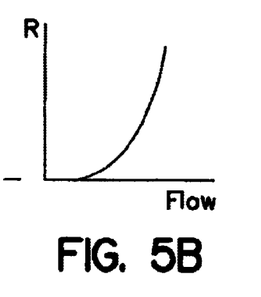

FIG. 5A shows a valving arrangement where the resistance increases with increasing flow rate. The proportionality of resistance to flow rate is shown in FIG. 5B. Such an arrangement allows for comfortable inhalation at the desired flow rate. As with the arrangement of FIG. 4A, the resistance at 10 liters per minute would be approximately 1 cm $H_2O^{1/2}/Lmin^{-1}$.

Figure 6A:
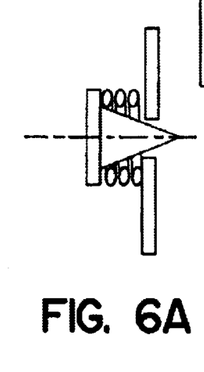
FIG. 6A is a perspective view of a valve that provides for decreasing resistance with increasing flow rate and FIG. 6B is a graph showing the type of resistance obtained therefrom.
Figure 6B:
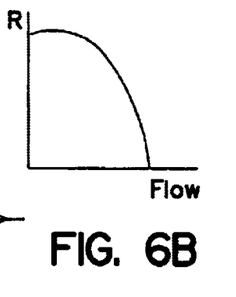

FIG. 6A shows a valving arrangement where the resistance decreases with increasing flow rate. This arrangement is useful where an aerosol bolus can be delivered slowly enough to ensure that it has entered the lower airway prior to the flow being allowed to increase to over 10 liters per minute. The proportionality of resistance to flow rate is shown in FIG. 6B.

Figure 7A:
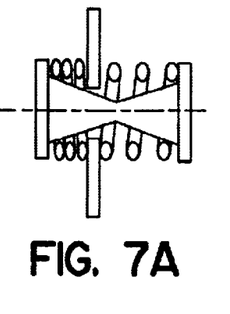
FIG. 7A is a perspective view of a valve that provides for high resistance at all flow rates except the desired flow rate and FIG. 7B is a graph showing the type of resistance obtained therefrom.
Figure 7B:
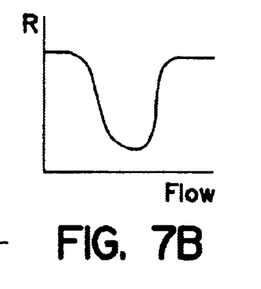

FIG. 7A shows a valving arrangement where the resistance is high at all flow rates except for the desired flow rate. The proportionality of resistance to flow rate is shown in FIG. 7B. The resistance at 10 liters per minute would be 0.25 cm $H_2O^{1/2}/Lmin^{-1}$ and greater than 1 cm $H_2O^{1/2}/Lmin^{-1}$ at other than the desired flow rate.

It is also possible, but somewhat less desirable to provide training to a patient using a device which is not restricted such that the patient learns to inspire at a flow rate at or below 10 liters per minute.

The following examples are illustrative of the present invention. It is not to be construed as limiting the scope of the invention. Variations and equivalents of this example will be apparent to those of skill in the art in light of the present disclosure, the drawings and the claims herein.

EXAMPLES

Materials and Methods

Materials

Crystalline human zinc insulin, 26.3 U/mg was obtained from Eli Lilly and Company, Indianapolis, Ind. and found to be >99% pure as measured by rpHPLC.

Human calcitonin was obtained from Ciba-Geigy.

Low molecular weight heparin sodium salt (average molecular weight ~6000) was obtained from Sigma Chemical, St. Louis, Mo.

Cyclosporin A, BMP grade was obtained as a powder crystallized from acetone (melting point 148–150° C.) from Poli Industria Chemica, S.p.A.

Human serum albumin (HSA) (Tentex Fr V, Low Endotoxin, Fatty Acid Free) was obtained from Miles Inc. (Kankakee, Ill.)

Albuterol sulfate was obtained from Profarmaco (Milano, Italy)

USP mannitol was obtained from Roquette Corporation (Gurnee, Ill.).

USP lactose was obtained from Spectrum (New Brunswick, N.J.).

Glycine was purchased from Sigma Chemical Company (St. Louis, Mo.).

Sodium citrate dihydrate, USP was obtained from J. T. Baker (Phillipsburg, N.J.).

Ethanol (200 proof, USP, NF grade) was obtained from Spectrum (New Brunswick, N.J.).

Powder Production

Insulin powders were made by dissolving bulk crystalline insulin in sodium citrate buffer containing mannitol and glycine to give final solids concentration of 7.5 mg/ml and pH of 6.7±0.3. The spray dryer was operated with an inlet temperature between 110° C. and 120° C. and a liquid feed rate of 5 m/min, resulting in an outlet temperature between 70° C. and 80° C. The solutions were then filtered through a 0.22 μm filter and spray dried in a Buchi Spray Dryer to form a fine white amorphous powder. The resulting powders were stored in tightly capped containers in a dry environment (<10% RH).

Powders containing 26.7% human calcitonin were made by spray drying an aqueous mixture containing human calcitonin. The mixture was prepared by combining 1.9 mg human calcitonin per 1.0 mL deionized water with 4.3 mg/mL mannitol and 0.9 mg/mL citrate buffer at a pH of 3.85. The mixture was spray dried in a Buchi Spray Dryer that was operated with an inlet temperature between 110° C. and 120° C. and a liquid feed rate of 5.5 ml/min, resulting in an outlet temperature between 70° C. and 80° C. Once the aqueous mixture was consumed, the outlet temperature was maintained at 80° C. for about 10 minutes by slowly decreasing the inlet temperature to provide a secondary drying. The resulting powders were stored in tightly capped containers in a dry environment (<10% RH).

Powders containing 93% low molecular weight (lmw) heparin powders were made by spray drying an aqueous mixture containing lmw heparin. The mixture was prepared by combining 6.9 mg lmw heparin per 1.0 mL deionized water with 0.5 mg/mL HSA a pH of 6.9. The mixture was spray dried in a Buchi Spray Dryer that was operated with an inlet temperature of 140° C. and a liquid feed rate of 3.8 ml/min, resulting in an outlet temperature of 85° C. Once the aqueous mixture was consumed, the outlet temperature was maintained at 80° C. for about 10 minutes by slowly decreasing the inlet temperature to provide a secondary drying. The resulting powders were stored in tightly capped containers in a dry environment (<10% RH).

Powders containing cyclosporin were made by spray drying an organic solution containing 1.5 g cyclosporin A and 50 mL ethanol. The solution was spray dried in a Buchi Spray Dryer using a nitrogen atmosphere containing less than 5% oxygen (with $N_2$ atm <5% $O_2$ that was operated with an inlet temperature of 100° C. and a liquid feed rate of 5 mL/min, resulting in an outlet temperature of 70° C. The resulting powders were stored in tightly capped containers in a dry environment (<10% RH).

Powders containing 2.3% albuterol sulfate were made by spray drying an aqueous mixture containing albuterol sulfate. The mixture was prepared by combining 0.60 mg albuterol sulfate and 25.68 mg lactose per 1.0 mL deionized water at a pH of 4.6. The mixture was spray dried in a Niro Spray Dryer that was operated with an inlet temperature of 120° C. and a liquid feed rate of 50 mL/min, resulting in an outlet temperature between 64.7° C. and 67.2° C. The resulting powders were stored in tightly capped containers in a dry environment (<10% RH).

Powder Analysis

The particle size distribution of the powders was measured by liquid centrifugal sedimentation in a Horiba CAPA-700 Particle Size Analyzer following dispersion of the powders in Sedisperse A-11 (Micrometrics, Norcross, Ga.). The moisture content of the powders was measured by the Karl Fischer technique using a Mitsubishi CA-06 Moisture Meter. The aerosol particle size distribution was measured using a cascade impactor (Graseby Andersen, Smyrna, Ga.). The delivered dose efficiency (DDE) is evaluated using the Inhale Therapeutic Systems' aerosol devices, similar to that described in WO96/09085. The DDE is defined as the percentage of the nominal dose contained within a blister package that exited the mouthpiece of the aerosol device and was captured on a glass fiber filter (Gelman, 47 mm diameter) through which a vacuum was drawn (30 L/min) for 2.5 seconds following device actuation. DDE was calculated by dividing the mass of the powder collected on the filter by the mass of the powder in the blister pack.

In the case of insulin, the integrity of insulin before and after powder processing was measured against a reference standard of human insulin by redissolving weighed portions of powder in distilled water and comparing the redissolved solution with the original solution put into the spray dryer. Retention time and peak area by rpHPLC were used to determine whether the insulin molecule had been chemically modified or degraded in the process. UV absorbance was used to determine insulin concentration (at 278 nm) and presence of absence of insoluble aggregates (at 400 nm). In addition, the pHs of the starting and reconstituted solutions were measured. The amorphous nature of the insulin powder was confirmed by polarized light microscopy.

In Vivo Testing

In order to examine the effect of changes in the rate of inhalation on the bioavailability of inhaled active agent, 12 individuals were dosed with insulin at the following peak sustained flow rates in a randomized sequence:

10 L/min±5 L/min

25 L/min±5 L/min

35 L/min or greater

Inhale Therapeutic Systems' (San Carlos, Calif.) dry powder inhaler was used to administer the aerosolized active agent powder. In the case of insulin, 3 mg of the amorphous insulin powders described above were filled into blister packages and inserted into the inhaler. The inhaler dispersed the powder and produced an aerosol cloud of medication which was held in a volume of approximately 240 ml in a holding chamber. The volume of the holding chamber was a minor fraction of a deep inspiratory breath (>2 liters). The chamber was designed so that during inhalation of the aerosol cloud, ambient air was pulled into the chamber thereby pushing the aerosol cloud out of the chamber and deep into the lungs. Each 3 mg dose of the dry powder contained 82.5 U of insulin.

The subjects were trained in the breathing maneuvers for inhalation of active agent. The steps were: (1) Subject exhaled to functional residual capacity and wrapped lips around the mouthpiece of the inhaler; (2) A cloud of aerosolized active agent was dispersed from the blister pack into the holding chamber of the inhaler; (3) Subject inhaled at the designated rate until total lung capacity was reached (this should have removed all of the aerosol from the chamber); (4) Subject removed mouth from the inhaler and held breath for 5 seconds; and (5) Subject exhaled gently to normal expiratory level and resumed normal breathing.

All subjects fasted at least eight (8) hours prior to insulin dosing and were required to refrain from lying down, eating or drinking caffeinated beverages during the first six (6) hours after dosing in order to standardize experimental conditions. Blood was collected at 30 and 15 minutes prior to insulin dosing; and 0 (just prior to insulin dosing), 5, 10, 20, 30, 45, 60, 90, 120, 180, 240, 300 and 360 minutes after the start of the inhalation.

Spirometery was performed on each subject prior to dosing to determine their pulmonary function. $FEV_1$ was at least 70% of predicted normal values. To determine whether inhalation of active agent powder caused bronchoconstriction or other change in pulmonary function, spirometry was also performed prior to and 30, 60 and 360 minutes after the start of each administration of active agent. At each time point, each subject performed 3 forced expiratory volume tests.

In order to obtain the appropriate inhaled flow rates, subjects were able to view the output from the inhalation measurement device and were instructed to try to match their inhalation rate to the desired rate on the output from the device. For the 10 L/min rate, inhalation lasted approximately 15 seconds. For the 25 L/min inhalation rate, inhalation required approximately 6 seconds. For the >35 L/min inhalation rate, the subjects were instructed to inhale as rapidly as possible.

Example 1

Insulin Powders

Insulin powders were prepared as described above and administered to patients also as described above. The bioavailibilities, peak insulin concentrations and time to peak insulin concentrations were as shown in Table I below.

The figures show, surprisingly, that inspiratory flow rates of 10 liters per minute or less achieved higher bioavailabilities of insulin (AUC), and higher peak concentrations of insulin (Cmax) than did inspiratory flow rates of 17.0 liters per minute or greater. Further, blood glucose level control (AUC) was greater for an inspiratory flow rate of 9.1 liters per minute than for the higher flow rates, and the maximum concentration (Cmax) was lower for the lower flow rate. Accordingly, a flow rate below 17 liters per minute, preferably 10 liters per minute or less is desired for optimal insulin delivery and glucose blood level control.

Example 2

Human Calcitonin Powders

Human calcitonin powders are prepared as described above. Upon administration to patients, flow rates below 17 liters per minute will result in higher bioavailabilities and lower times to peak concentration than those above 17 liters per minutes.

Example 3

Heparin Powders

Low molecular weight heparin powders are prepared as described above. Upon administration to patients, flow rates below 17 liters per minute will result in higher bioavailabilities and lower times to peak concentration than those above 17 liters per minutes.

Example 4

Cyclosporin Powders

Cyclosporin A powders are prepared as described above. Upon administration to patients, flow rates below 17 liters per minute will result in higher lung deposition and thus increased therapeutic effect than those above 17 liters per minutes.

Example 5

Albuterol Sulfate Powders

Albuterol sulfate powders are prepared as described above. Upon administration to patients, flow rates below 17 liters per minute will result in higher lung deposition and thus increased therapeutic effect than those above 17 liters per minutes The disclosure of each publication, patent or patent application mentioned in this specification is incorporated by reference herein to the same extent as if each individual publication, patent or patent application were specifically and individually indicated to be incorporated by reference.

We claim:

1. A device for increasing the bioavailability of an aerosolized active agent, said device comprising a flow restrictor for limiting the flow of an aerosolized active agent formulation to a human patient to less than 17 liters per minute, wherein the device is adapted to aerosolize the active agent formulation and wherein the active agent formulation is (i) a powder, (ii) a solution, suspension, or slurry that may be nebulized, or (iii) suspended or dissolved in a propellant.

TABLE 1

Summary of Pharmacokinetics and Pharmacodynamic Factors for Insulin aerosol inhaled at Different Inspiratoy Flow rates.

| Peak sustained flow rate [l/min] | Average flow during aerosol administration [l/min] | Insulin values | | | Glucose values | | |
|---|---|---|---|---|---|---|---|
| | | $t_{max}$ [min] | $C_{max}$ [mU/ml] | $AUC_{0-360\,mm}$ [mU.min/ml] | $t_{max}$ [min] | $C_{max}$ [mU/ml] | $AUC_{0-360\,mm}$ [mU.min/ml] |
| >35 | 21.1 ± 4.5 | 48.8 ± 13.0 | 21.0 ± 8.0 | 2052 ± 1342 | 28.7 ± 6.6 | 77.5 ± 29.2 | 5588 ± 747 |
| ≅25 | 17.0 ± 4.9 | 46.3 ± 26.0 | 21.7 ± 7.4 | 2555 ± 873 | 30.9 ± 12.8 | 91.3 ± 28.9 | 5461 ± 2931 |
| ≅10 | 9.1 ± 1.7 | 41.7 ± 8.1 | 31.6 ± 16.0 | 3502 ± 1342 | 38.8 ± 13.2 | 67.5 ± 17.5 | 6230 ± 1908 |

2. The device of claim 1 wherein the flow restrictor comprises an orifice.

3. The device of claim 1 wherein the flow restrictor comprises apertures of 0.5 to 0.9 mm in diameter.

4. The device of claim 1 wherein the flow restrictor is a valve that provides for decreasing resistance with increasing flow rate.

5. The device of claim 1 wherein the flow restrictor is a valve that provides for high resistance at all flow rates except a desired flow rate range.

6. The device of claim 1 wherein the device is adapted to be used with an active agent selected from the group consisting of insulin, cyclosporin, parathyroid hormone, follicle stimulating hormone, alpha-1-antitrypsin, budesonide, human growth hormone, growth hormone releasing hormone, interferon alpha, interferon beta, growth colony stimulating factor, leutinizing hormone releasing hormone, calcitonin, low molecular weight heparin, somatostatin, respiratory syncytial virus antibody, erythropoietin, Factor VIII, Factor IX, ceredase, cerezyme and analogues, agonists and antagonists thereof.

7. The device of claim 1 wherein the active agent formulation is a powder and wherein the device is adapted to aerosolize the active agent formulation.

8. The device of claim 1 wherein the active agent formulation is contained in a blister and wherein the device is adapted to receive the blister.

9. The device of claim 1 wherein the device is adapted to aerosolize a powder active agent formulation.

10. The device of claim 9 wherein the device is adapted to aerosolize the powder active agent formulation using compressed air.

11. A device for delivering an active agent to the lungs of a human patient, said device comprising a flow restrictor for limiting the flow of an aerosolized active agent formulation to less than 17 liters per minute, wherein the flow restrictor is a valve that provides for increasing resistance with increasing flow rate.

12. A device for delivering aerosolized insulin to the lungs of a human patient, wherein said device comprises a flow resirictor to restrict an inspiratory flow rate of an aerosolized insulin formulation to less than 17 liters per minute and wherein the device is adapted to aerosolize the insulin.

13. The device of claim 12 wherein the inspiratory flow rate is 10 liters per minute or less.

14. The device of claim 12 wherein the active agent formulation is a powder and wherein the device is adapted to aerosolize the active agent formulation.

15. The device of claim 12 wherein the active agent formulation is contained in a blister and wherein the device is adapted to receive the blister.

16. A device for delivering an aerosolized active agent to the lungs of a human patient, wherein said device comprises one or more orifices sized so that an aerosolized active agent formulation may be delivered at an inspiratory flow rate of less than 17 liters per minute, wherein the device is adapted to aerosolize the active agent formulation and wherein the active agent formulation is (i) a powder, (ii) a solution, suspension, or slurry that may be nebulized, or (iii) suspended or dissolved in a propellant.

17. The device of claim 12 wherein the device is adapted to deliver an aerosolized insulin formulation to the lungs.

18. The device of claim 16 wherein the orifices are sized so that the aerosolized active agent formulation may be delivered at an inspiratory flow rate of 10 liters per minute or less.

19. The device of claim 16 wherein the active agent formulation is a powder and wherein the device is adapted to aerosolize the active agent formulation.

20. The device of claim 16 wherein the active agent formulation is contained in a blister and wherein the device is adapted to receive the blister.

21. A device for delivering an active agent to the lungs of a human patient, said device comprising:

a chamber in flow communication with a mouthpiece; and means for limiting an inspiratory flow rate through the mouthpiece to less than 17 liters per minute, whereby an acrosolized active agent formulation in the chamber may be delivered to the human patient, the active agent formulation being (i) a powder, (ii) a solution, suspension, or slurry that may be nebulized, or (iii) suspended or dissolved in a propellant.

22. The device of claim 21 wherein the inspiratory flow rate is limited to 10 liters per minute or less.

23. The device of claim 21 wherein the device is adapted to deliver an aerosolized insulin formulation to the lungs.

24. The device of claim 21 wherein the active agent formulation is a powder and wherein the device is adapted to aerosolize the active agent formulation.

25. The device of claim 21 wherein the active agent formulation is contained in a blister and wherein the device is adapted to receive the blister.

* * * * *

UNITED STATES PATENT AND TRADEMARK OFFICE
CERTIFICATE OF CORRECTION

PATENT NO.    : 6,655,379 B2
DATED         : December 2, 2003
INVENTOR(S)   : Andrew Clark et al.

It is certified that error appears in the above-identified patent and that said Letters Patent is hereby corrected as shown below:

<u>Column 12, lines 42 - Column 14, line 46,</u>
Replace Claims 1-25 with the following:

1. A device for increasing the bioavailability of an aerosolized active agent, said device comprising a flow restrictor which provides a variable flow resistance for limiting the flow of an aerosolized active agent formulation to a human patient to less than 17 liters per minute, wherein the device is adapted to aerosolize the active agent formulation and wherein the active agent formulation is (i) a powder, (ii) a solution, suspension, or slurry that may be nebulized, or (iii) suspended or dissolved in a propellant.

2. The device of claim 1 wherein the flow restrictor comprises an orifice.

3. The device of claim 2 wherein the flow restrictor comprises apertures of 0.5 to 0.9 mm in diameter.

4. The device of claim 1 wherein the flow restrictor is a valve that provides for decreasing resistance with increasing flow rate.

5. The device of claim 1 wherein the flow restrictor is a valve that provides for high resistance at all flow rates except a desired flow rate range.

6. The device of claim 1 wherein the device is adapted to be used with an active agent selected from the group consisting of insulin, cyclosporin, parathyroid hormone, follicle stimulating hormone, alpha-1-antitrypsin, budesonide, human growth hormone, growth hormone releasing hormone, interferon alpha, interferon beta, growth colony stimulating factor, leutinizing hormone releasing hormone, calcitonin, low molecular weight heparin, somatostatin, respiratory syncytial virus antibody, erythropoietin, Factor VIII, Factor IX, ceredase, cerezyme and analogues, agonists and antagonists thereof.

7. The device of claim 1 wherein the active agent formulation is a powder and wherein the device is adapted to aerosolize the active agent formulation.

8. The device of claim 1 wherein the active agent formulation is contained in a blister and wherein the device is adapted to receive the blister.

9. The device of claim 1 wherein the device is adapted to aerosolize a powder active agent formulation 10. The device of claim 9 wherein the device is adapted to aerosolize the powder active agent formulation using compressed air.

11. A device for delivering an active agent to the lungs of a human patient, said device comprising a flow restrictor for limiting the flow of an aerosolized active agent formulation, wherein the flow restrictor is a valve that varies the flow resistance to limit the flow to a rate less than 17 liters per minute 12. A device for delivering aerosolized insulin to the lungs of a human patient, wherein said device comprises a flow restrictor which provides a variable flow resistance to restrict an inspiratory flow rate of an aerosolized insulin formulation to less than 17 liters per minute and wherein the device is adapted to aerosolize the insulin.

13. The device of claim 12 wherein the flow restrictor provides a variable flow resistance to restrict the inspiratory flow rate to 10 liters per minute or less.

14. The device of claim 12 wherein the active agent formulation is a powder and wherein the device is adapted to aerosolize the active agent formulation.

15. The device of claim 12 wherein the active agent formulation is contained in a blister and wherein the device is adapted to receive the blister.

16. A device for delivering an aerosolized active agent to the lungs of a human patient, wherein said device comprises an orifice that varies in size so that an aerosolized active agent formulation may be delivered at an inspiratory flow rate of less than 17 liters per minute, wherein the device is adapted to aerosolize the active agent formulation and wherein the active agent formulation is (i) a powder, (ii) a solution, suspension, or slurry that may be nebulized, or (iii) suspended or dissolved in a propellant.

17. The device of claim 16 wherein the device is adapted to deliver an aerosolized insulin formulation to the lungs.

18. The device of claim 16 wherein the orifice varies in size so that the aerosolized active agent formulation may be delivered at an inspiratory flow rate of 10 liters per minute or less.

19. The device of claim 16 wherein the active agent formulation is a powder and wherein the device is adapted to aerosolize the active agent formulation.

UNITED STATES PATENT AND TRADEMARK OFFICE
CERTIFICATE OF CORRECTION

PATENT NO.    : 6,655,379 B2
DATED         : December 2, 2003
INVENTOR(S)   : Andrew Clark et al.

It is certified that error appears in the above-identified patent and that said Letters Patent is hereby corrected as shown below:

<u>Column 12, lines 42 - Column 14, line 46 (cont'd),</u>

20. The device of claim 16 wherein the active agent formulation is contained in a blister and wherein the device is adapted to receive the blister.

21. A device for delivering an aerosolized active agent to the lungs of a human patient, said device comprising:
    a chamber in flow communication with a mouthpiece;
    means for aerosolizing the active agent; and
    means for varying the flow resistance to limit an inspiratory flow rate through the mouthpiece to less than 17 liters per minute,
    whereby an aerosolized active agent formulation in